United States Patent
Willis

(10) Patent No.: US 7,720,520 B2
(45) Date of Patent: May 18, 2010

(54) METHOD AND SYSTEM FOR REGISTERING AN IMAGE WITH A NAVIGATION REFERENCE CATHETER

(75) Inventor: N. Parker Willis, Atherton, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1407 days.

(21) Appl. No.: 11/002,399

(22) Filed: Dec. 1, 2004

(65) Prior Publication Data
US 2006/0116575 A1 Jun. 1, 2006

(51) Int. Cl.
*A61B 5/05* (2006.01)
*A61B 8/14* (2006.01)
*A61B 5/04* (2006.01)
*A61B 6/00* (2006.01)

(52) U.S. Cl. ............. 600/424; 600/471; 600/374; 378/4; 111/111

(58) Field of Classification Search ........... 600/471, 600/374, 424; 607/122; 378/4
See application file for complete search history.

(56) References Cited

U.S. PATENT DOCUMENTS

| | | | |
|---|---|---|---|
| 5,391,199 A | | 2/1995 | Ben-Haim |
| 5,443,489 A | * | 8/1995 | Ben-Haim .............. 607/115 |
| 6,019,725 A | * | 2/2000 | Vesely et al. ........... 600/447 |
| 6,216,027 B1 | * | 4/2001 | Willis et al. ............ 600/424 |
| 6,259,941 B1 | | 7/2001 | Chia et al. |
| 6,298,257 B1 | | 10/2001 | Hall et al. |
| 6,490,474 B1 | * | 12/2002 | Willis et al. ........... 600/424 |
| 6,574,498 B1 | | 6/2003 | Gilboa |
| 6,711,429 B1 | * | 3/2004 | Gilboa et al. ........... 600/407 |
| 6,788,967 B2 | | 9/2004 | Ben-Haim et al. |
| 7,366,562 B2 | * | 4/2008 | Dukesherer et al. ..... 600/424 |

(Continued)

FOREIGN PATENT DOCUMENTS

WO WO 2004/060158 A1 7/2004

OTHER PUBLICATIONS

PCT International Preliminary Report on Patentability (Chapter I of the Patent Cooperation Treaty) for PCT/US2005/043186, Applicant: Boston Scientific Scimed, Inc., Form PCT/IB/326, dated Jun. 14, 2007 (8 pages.).

(Continued)

*Primary Examiner*—Eric F Winakur
*Assistant Examiner*—Katherine L Fernandez
(74) *Attorney, Agent, or Firm*—Vista IP Law Group LLP

(57) ABSTRACT

Methods and systems for processing and/or superimposing a medical image of an anatomical body (e.g., a heart) with graphical information are provided. Reference elements and/or reference catheter are placed in contact with the anatomical body. A physical structure within a navigational coordinate system is located using the reference elements and/or reference catheter. An image reference within an image coordinate corresponding to the physical structure is located. Location of the image reference can be accomplished, e.g., by displaying the medical image and electronically marking the displayed image reference, or by automatically locating image data corresponding to the image reference. The navigational and image coordinate systems are then registered based on the location of the physical structure within the navigational coordinate system and the location of the image reference within the image coordinate system, which allows graphical information to be accurately merged with the medical image data.

61 Claims, 6 Drawing Sheets

U.S. PATENT DOCUMENTS

2003/0158477 A1* 8/2003 Panescu ............ 600/424
2004/0236220 A1 11/2004 Willis
2006/0122514 A1* 6/2006 Byrd et al. ............ 600/466

OTHER PUBLICATIONS

Atul Verma, M.D., Novel Method to Integrate Three-Dimensional Computed Tomographic Images of the Left Atrium with Real-Time Electroanatomic Mapping, J. Cardiovac Electrophysiol., vol. 5, p. 1, Aug. 2004, Cleveland, OH.

PCT International Search Report for PCT/US2005/043186, Applicant: Boston Scientific Scimed, Inc., Form PCT/ISA/210 and 220, dated Jul. 20, 2006 (6 pages).

PCT Written Opinion of the International Search Authority for PCT/US2005/043186, Applicant: Boston Scientific Scimed, Inc., Form PCT/ISA/237, dated Jul. 20, 2006 (6 pages).

* cited by examiner

RECEIVE

| | TXVR1 | TXVR2 | TXVR3 | TXVR4 | TXVR5 | TXVR6 | TXVR7 | TXVR8 | RX1 | RX2 | RX3 |
|---|---|---|---|---|---|---|---|---|---|---|---|
| TXVR1 | X | d1 | d2 | d3 | d4 | d5 | d6 | d7 | d8 | d9 | d10 |
| TXVR2 | d11 | X | d12 | d13 | d14 | d15 | d16 | d17 | d18 | d19 | d20 |
| TXVR3 | d21 | d22 | X | d23 | d24 | d25 | d26 | d27 | d28 | d29 | d30 |
| TXVR4 | d31 | d32 | d33 | X | d34 | d35 | d36 | d37 | d38 | d39 | d40 |
| TXVR5 | d41 | d42 | d43 | d44 | X | d45 | d46 | d47 | d48 | d49 | d50 |
| TXVR6 | d51 | d52 | d53 | d54 | d55 | X | d56 | d57 | d58 | d59 | d60 |
| TXVR7 | d61 | d62 | d63 | d64 | d65 | d66 | X | d67 | d68 | d69 | d70 |
| TXVR8 | d71 | d72 | d73 | d74 | d75 | d76 | d77 | X | d78 | d79 | d80 |

TRANSMIT

METHOD AND SYSTEM FOR REGISTERING AN IMAGE WITH A NAVIGATION REFERENCE CATHETER

FIELD OF THE INVENTION

The present inventions generally relate to medical probes, and more particularly to systems and methods for navigating catheters within anatomical organs or other anatomical structures.

BACKGROUND OF THE INVENTION

It is often necessary or desirable to determine the location of a medical probe relative to a location of interest within three-dimensional space. In many procedures, such as interventional cardiac electrophysiology therapy, it is important for the physician to know the location of a probe, such as a catheter, (especially, a therapeutic catheter) relative to the patient's internal anatomy. During these procedures, a physician, e.g., steers an electrophysiology mapping catheter through a main vein or artery into the interior region of the heart that is to be treated. The physician then determines the source of the cardiac rhythm disturbance (i.e., the targeted cardiac tissue) by placing mapping elements carried by the catheter into contact with the heart tissue, and operating the mapping catheter to generate an electrophysiology map of the interior region of the heart. Having identified the targeted cardiac tissue, the physician then steers an ablation catheter (which may or may not be the same catheter as the mapping catheter above) into the heart and places an ablating element carried by the catheter tip near the targeted cardiac tissue, and directs energy from the ablating element to ablate the tissue and form a lesion, thereby treating the cardiac disturbance.

Traditionally, navigation of catheters relative to points of interest has been accomplished using fluoroscopy. In this case, radiopaque elements are located on the distal end of the catheter and fluoroscopically imaged as the catheter is routed through the body. As a result, a two-dimensional image of the catheter, as represented by the illuminated radiopaque elements, is generated, thereby allowing the physician to roughly determine the location of the catheter. The use of fluoroscopy in locating catheters is somewhat limited, however, in that the physician is only able to visualize the catheter and surrounding tissues in two dimensions. In addition, fluoroscopy does not image soft tissues, making it difficult for the physician to visualize features of the anatomy as a reference for the navigation. Thus, fluoroscopy is sub-optimal for the purpose of navigating a catheter relative to anatomical structure composed primarily of soft tissues, e.g., within the heart.

Various types of three-dimensional medical systems (e.g., the Realtime Position Management™ (RPM) tracking system, developed commercially by Boston Scientific Corporation and described in U.S. Pat. No. 6,216,027 and U.S. patent application Ser. No. 09/128,304, entitled "A Dynamically Alterable Three-Dimensional Graphical Model of a Body Region," and the CARTO EP Medical system, developed commercially by Biosense Webster and described in U.S. Pat. No. 5,391,199), have been developed, or at least conceived, to address this issue. In these medical systems, a graphical representation of the catheter or a portion thereof is displayed in a three-dimensional computer-generated representation of a body tissue, e.g., a heart chamber. The three-dimensional representation of the body tissue is produced by mapping the geometry of the inner surface of the body tissue in a three-dimensional coordinate system, e.g., by moving a mapping device to multiple points on the body tissue. The position of the device to be guided within the body tissue is determined by placing one or more location elements on the device and tracking the position of these elements within the three-dimensional coordinate system. An electrophysiological map generated from information acquired by the mapping device can also be graphically displayed.

The main difference between the RPM tracking system and the CARTO EP system is that the latter establishes an external coordinate system using magnetic transmitters located outside of the patient's body, whereas the former establishes an internal coordinate system using ultrasound transceivers mounted on reference catheters that are located within the heart itself. Because the measurements taken by the CARTO EP system are performed in an external coordinate system, magnetic sensors must be attached to the patient or within the patient, such as on a reference catheter placed within the heart, so that inadvertent movement of the patient (e.g., movement caused by respiration and/or patient shifting (heart pumping is compensated by gating)) may be compensated for when measuring the location of the mapping device and other devices to be tracked. In contrast, because the measurements taken by the RPM tracking system are performed in an internal coordinate system, which self-compensates as the patient moves (i.e., the internal coordinate system moves as the patient moves), no additional sensors are needed.

Although the uses of the RPM tracking system and CARTO EP system have, to a large extent, been successful in facilitating the navigation of catheters within the cavities of the heart, the graphical representations of the heart chambers lack the resolution produced by conventional imaging systems, such as Computed Tomography (CT) and Magnetic Resonance Imaging (MRI) systems. This lack of resolution especially impacts the navigation of catheters within and around the complex anatomy of the left atrium and pulmonary veins. In order to more accurately localize catheters, enhance the efficacy of ablative lesions, and reduce procedure time, it has been suggested that high resolution preoperative images, such as those generated by CT and MRI systems, could be merged with three-dimensional graphical information, such as electrophysiological maps and catheter representations.

For example, Biosense Webster has developed a software package, referred to as Cartomerge™, which provides the CARTO EP system with the capability of merging three-dimensional CT images with electrophysiological mapping data. This integrated system requires the user to merge the CT image with the electrophysiological map by matching corresponding anatomical reference points on the image and map. Besides requiring an additional step to be performed by the user, the image integration is only as accurate as that of the anatomical envelope of the electrophysiological map, which as discussed above, lacks the resolution typically seen in a CT image. As such, catheter localization relative to the CT image may be inaccurate to a certain extent. Also, this system requires some type of graphical representation of the heart to be displayed prior to the image merging step, so that the anatomical reference points can be matched. Thus, the CT image cannot be used when initially navigating the catheter within the heart. In addition, integration of the CT image is accomplished within an external coordinate system, thereby requiring additional sensors and/or catheters to compensate for patient movement.

There thus remains a need for a self-compensating system and method that automatically integrates a medical image, such as a CT or MRI image, with a graphical information, such as an electrophysiological map and/or catheter representations.

SUMMARY OF THE INVENTION

The present inventions are directed to methods and systems for processing and/or superimposing a medical image of an anatomical body (e.g., a heart) with graphical information using reference elements and/or reference catheters to both establish a navigational or graphical coordinate system and for registering the medical image with the navigational or graphical coordinate system. The medical image may be any image that has been generated by an imaging modality, but preferably is a relatively high-resolution image, such as a Computed Tomography (CT) image. The medical image is typically acquired as a pre-operative image, but may also be acquired during a medical procedure, in which case, the systems may comprise an imaging subsystem. The medical image will be arranged in an image coordinate system, which will most often be a three-dimensional image coordinate system.

In accordance with a first aspect of the present inventions, a method of processing the medical image comprises placing a plurality of reference elements into contact with an anatomical body. The reference elements may be located within the anatomical body, but can also be located on the exterior of the anatomical body depending on the nature of the medical procedure to be performed. For example, if the anatomical body is the heart, the reference elements may be placed in the coronary sinus of the heart, which can technically be considered to be located on the exterior of the heart. Significantly, the location will be selected such that the reference elements are placed in a stable relationship with the anatomical structure. In the preferred method, the reference elements are carried by at least one reference catheter to facilitate their delivery and stability in relation to the anatomical body, but can also be placed in contact with the anatomical structure without the use of catheters as desired.

The method further comprises transmitting signals between the reference elements to establish a navigational coordinate system internal to the anatomical body. Because the reference elements are located on the anatomical structure, the navigational coordinate system will be self-compensating in that the anatomical body may move without having to compensate for such movement using other means. In the preferred method, the navigational coordinate system is a three-dimensional coordinate system, but may be a two-dimensional coordinate system, or even a four-dimensional coordinate system (three dimensions in space and one dimension in time). In the preferred method, the reference elements take the form of ultrasound transducers, in which case, the transmitted signals will be ultrasound pulses. Alternatively, other signaling means, such as magnetic or electric, can be used. In the preferred method, the navigational coordinate system is established based on the times-of-flight of the transmitted signals. However, other characteristics (such as magnitude, phase, etc.) of the transmitted signals can be used to establish the navigational coordinate system.

The method further comprises determining the location of a physical structure within the navigational coordinate system, e.g., based on the locations of the reference elements within the navigational coordinate system, and determining the location of an image reference within the image coordinate corresponding to the physical structure. The physical structure may be the anatomical structure, or alternatively one or more of the reference elements in the case where the medical image contains the reference elements. Location of the image reference can be accomplished, e.g., by displaying the medical image and electronically marking the displayed image reference, or by automatically identifying image data corresponding to the image reference.

The method also comprises registering the navigational and image coordinate systems based on the determined location of the physical structure within the navigational coordinate system and the determined location of the image reference within the image coordinate system. For example, the coordinate system registration may be accomplished by calculating a coordinate transformation function and applying the coordinate transformation function to one of the image and navigational coordinate systems. The method may optionally comprise moving a catheter within the anatomical body, and transmitting signals between a location element carried by the catheter and the reference elements to determine the location of the catheter within the navigational coordinate system.

Registration of the navigational and image coordinate systems can be made more accurate by correlating another physical structure with a location element. For example, the method may optionally comprise moving a location element within the anatomical body, and transmitting signals between the reference elements and the location element to determine the location of the location element within the navigational coordinate system. The method may further comprise determining the location of the other physical structure within the navigational coordinate system based on the determined location of the location element within the navigational coordinate system, and determining the location of another image reference corresponding to the other physical structure within the image coordinate system. Registration of the navigational and image coordinate systems can be further based on the determined location of the other physical structure within the navigational coordinate system and the determined location of the other image reference within the image coordinate system.

In accordance with a second aspect of the present inventions, a medical system for processing the medical image is provided. The system comprises one or more catheters carrying a plurality of reference elements, and control circuitry (e.g., ranging circuitry) configured for conditioning the reference elements to transmit signals between each other. The reference elements may be ultrasound transducers, in which case, the transmitted signals will be ultrasound pulses.

The system further comprises one or more processors configured for establishing a navigational coordinate system based on the transmitted signals, locating a physical structure within the navigational coordinate system, locating an image reference within the image coordinate system corresponding to the physical structure, and registering the image and navigational coordinate systems based on the location of the image reference within the image coordinate system and the location of the physical structure within the navigational coordinate system. These functions can be performed in the same manner described above.

The system may optionally comprise a functional catheter carrying a location element, and the control circuitry can be configured for conditioning the location and reference elements to transmit signals between each other. In this case, the one or more processors can be configured for determining the location of the functional catheter within the navigational coordinate system based on the transmitted signals. Registration of the navigational and image coordinate systems can be made more accurate as described by correlating another physical structure with the location element in the manner described above.

In accordance with a third aspect of the present inventions, a method of superimposing the medical image and graphical information is provided. The method comprises placing a reference catheter in contact with the anatomical body. For example, if the anatomical body is a heart, the reference catheter can be placed within the coronary sinus. The method further comprises moving a functional catheter within the anatomical body, acquiring location information with the functional catheter by transmitting signals between the reference and functional catheters, and generating graphical information (e.g., a graphical representation of the catheter(s)) based on the location information. The nature of the signals can be ultrasonic, and the location information can be based on times-of-flight of the signals, as previously described. Optionally, the functional catheter may be moved around within the anatomical body, and the location information acquired during movement of the functional catheter within the anatomical body. Medical information, such as electrophysiology (EP) data, can be acquired with the functional catheter, and the graphical information (e.g., an EP map) generated from the acquired medical information.

The method further comprises locating a physical structure spatially correlated to the reference catheter. For example, the physical structure may be the anatomical structure, in which case, spatial correlation with the reference catheter is accomplished by virtue of their contact with each other, or the physical structure may be a portion of the reference catheter itself. Notably, this method allows the graphical information to be generated subsequent to the location of the physical structure, although the graphical information can be generated prior thereto as well. The method further comprises identifying an image reference corresponding to the physical structure. This can be accomplished in the same manners described above. The method further comprises merging the graphical information and medical image based on the located physical structure and the identified image reference. For example, graphical information and medical image can be merged by registering the graphical and image coordinate systems in the manner described above and then combining the registered graphical information and image data.

Registration and merger of the graphical information and image data can be made more accurate by correlating another physical structure with the functional catheter. For example, the method may comprise locating the other physical structure spatially correlated to the functional catheter, identifying another image reference corresponding to the other physical structure, and merging the graphical information and medical image further based on the other located physical structure and the other identified image reference.

In accordance with a fourth aspect of the present inventions, a medical system for superimposing the medical image and graphical information is provided. The system comprises a reference catheter, a functional catheter, and control circuitry (e.g., ranging circuitry) configured for conditioning the reference and functional catheters to transmit signals (e.g., ultrasound pulses) between each other. The system further comprises one or more processors configured for acquiring location information with the functional catheter based on the transmitted signals, locating a physical structure spatially correlated to the reference catheter, generating the graphical information based on the location information, identifying an image reference corresponding to the physical structure, and merging the graphical information and medical image based on the located physical structure and the identified image reference. These functions can be performed in the same manner described above. Registration and merger of the graphical information and medical image can be made more accurate as described by correlating another physical structure with the functional catheter in the manner described above.

In accordance with additional aspects of the present inventions, methods and medical systems for processing the medical image and/or superimposing the medical image and graphical information, are provided. These methods and systems are similar to those methods and systems described above, with the exception that the reference element(s) and/or reference catheter need not be used to establish a navigational coordinate system or otherwise used to communicate with location elements or catheters. However, the methods and systems in accordance with these additional aspects of the present inventions do require that image reference be identified by automatically analyzing the image data to identify reference data corresponding to the physical structure, which is then used to register the coordinate systems. Thus, any errors and time expended as a result of a manual process of identifying a reference with the medical image is eliminated or at least minimized.

Other objects and features of the present invention will become apparent from consideration of the following description taken in conjunction with the accompanying drawings.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
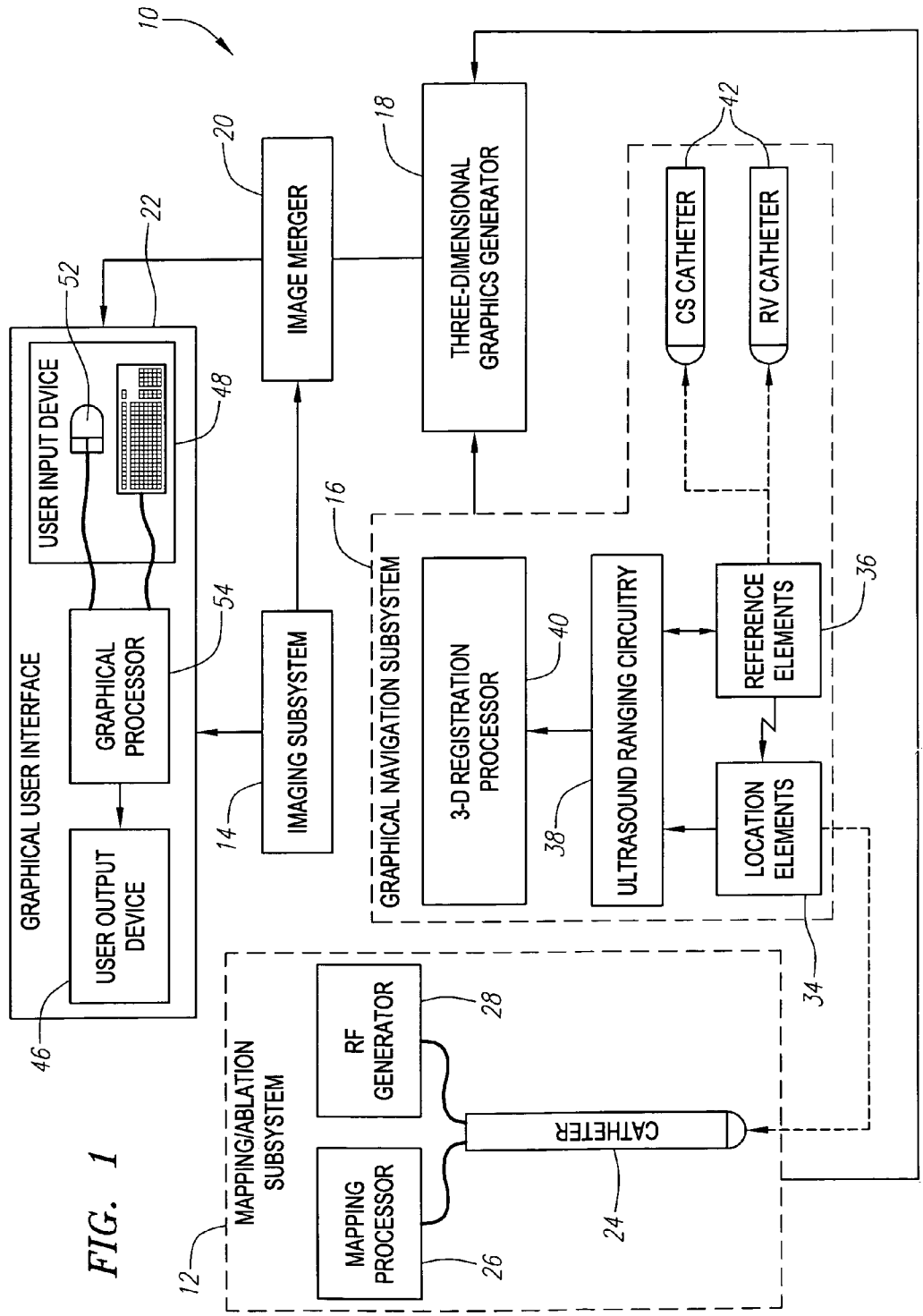
FIG. 1 is a functional block diagram of one preferred embodiment of a medical system constructed in accordance with the present inventions.

Referring to FIG. 1, an exemplary medical system 10 constructed in accordance with the present invention is shown. The medical system 10 is particularly suited for mapping and treating a heart (shown in FIGS. 2 and 3). Nevertheless, it should be appreciated that it can be used for treating, diagnosing, or otherwise displaying other anatomical bodies, such as the prostate, brain, gall bladder, uterus, esophagus, and other regions of the body.

The medical system 10 generally comprises (1) a mapping/ablation subsystem 12 for mapping and ablating tissue within the heart; (2) an imaging subsystem 14 for generating a high-resolution medical image of the heart; (3) a graphical navigation subsystem 16 for registering mapping data and the movement of medical devices within a three-dimensional navigational coordinate system (which in the illustrated embodiment, may also be referred to as a graphical coordinate system); (4) a three-dimensional graphics generator 18 for generating graphical information within the navigational coordinate system; (5) an image merger 20 for merging the medical image generated by the imaging subsystem 14 and the graphical information generated by the graphics generator 18 into a composite image; and (6) a graphical user interface 22 for displaying the composite image and other graphical information in response to user input.

It should be noted that the elements illustrated in FIG. 1 are functional in nature, and are not meant to limit the structure that performs these functions in any manner. For example, several of the functional blocks can be embodied in a single device, or one of the functional blocks can be embodied in multiple devices. Also, the functions can be performed in hardware, software, or firmware. It should also be noted that the elements illustrated in FIG. 1 may be centralized or distributed. For example, it is often the case that medical images of anatomical bodies are acquired at a different site than where the medical procedure is actually performed, in which case, the system 10 will be somewhat distributed to the extent that the imaging subsystem 14 will be provided at a different site than the remaining elements of the medical system 10.

I. Mapping/Ablation Subsystem

The mapping/ablation subsystem 12 is configured for identifying and treating a target tissue site or sites, e.g., aberrant conductive pathways. To this end, the mapping/ablation subsystem 12 comprises a mapping/ablation catheter 24, a mapping processor 26, and a radio frequency (RF) generator 28. As further illustrated in FIG. 2, the mapping/ablation catheter 24 comprises an elongate catheter member 30, a plurality of electrodes 32 (in this case, four) carried at the distal end of the catheter member 30, and a handle (not shown) carried at the proximal end of the elongate member 30. All four electrodes 32 on the catheter member 30 are configured to detect electrical signals in myocardial tissue for subsequent identification of target sites. The electrode 32 at the distal tip of the catheter member 30 is also configured to be used as an ablation electrode to provide ablation energy to the targeted sites when placed adjacent thereto and operated. The handle includes an electrical connector (not shown) for electrical coupling to the mapping processor 26 and RF generator 28.

Referring back to FIG. 1, the mapping processor 26 is configured to derive activation times and voltage distribution from the electrical signals obtained from the electrodes 32 to determine irregular electrical signals within the heart, which can then be graphically displayed as a map. Mapping of tissue within the heart is well known in the art, and thus for purposes of brevity, the mapping processor 26 will not be described in further detail. Further details regarding electrophysiology mapping are provided in U.S. Pat. Nos. 5,485,849, 5,494,042, 5,833,621, and 6,101,409, which are expressly incorporated herein by reference.

The RF generator 28 is configured to deliver ablation energy to the ablation electrode (i.e., the distal most electrode 32) in a controlled manner in order to ablate sites identified by the mapping processor 26. Alternatively, other types of ablative sources besides the RF generator 28 can be used, e.g., a microwave generator, an acoustic generator, a cryoablation generator, and a laser or other optical generator. Ablation of tissue within the heart is well known in the art, and thus for purposes of brevity, the RF generator 28 will not be described in further detail. Further details regarding RF generators are provided in U.S. Pat. No. 5,383,874, which is expressly incorporated herein by reference.

It should be noted that other types of mapping/ablation catheters can be used in the medical system 10. For example, a catheter having a basket structure of resilient splines, each of which carries a plurality of dedicated mapping electrodes can be used. This catheter may be placed in a heart chamber, so that the resilient splines conform to the endocardial surface of the heart, thereby placing and distributing the mapping electrodes along the entire endocardial surface of the cavity for efficient mapping. The catheter may also have a roving ablation electrode that can be steered in contact with the ablation sites identified by the mapping electrodes. Or a separate ablation catheter with a dedicated ablation electrode or electrodes can be used.

II. Imaging Subsystem

Figure 7:
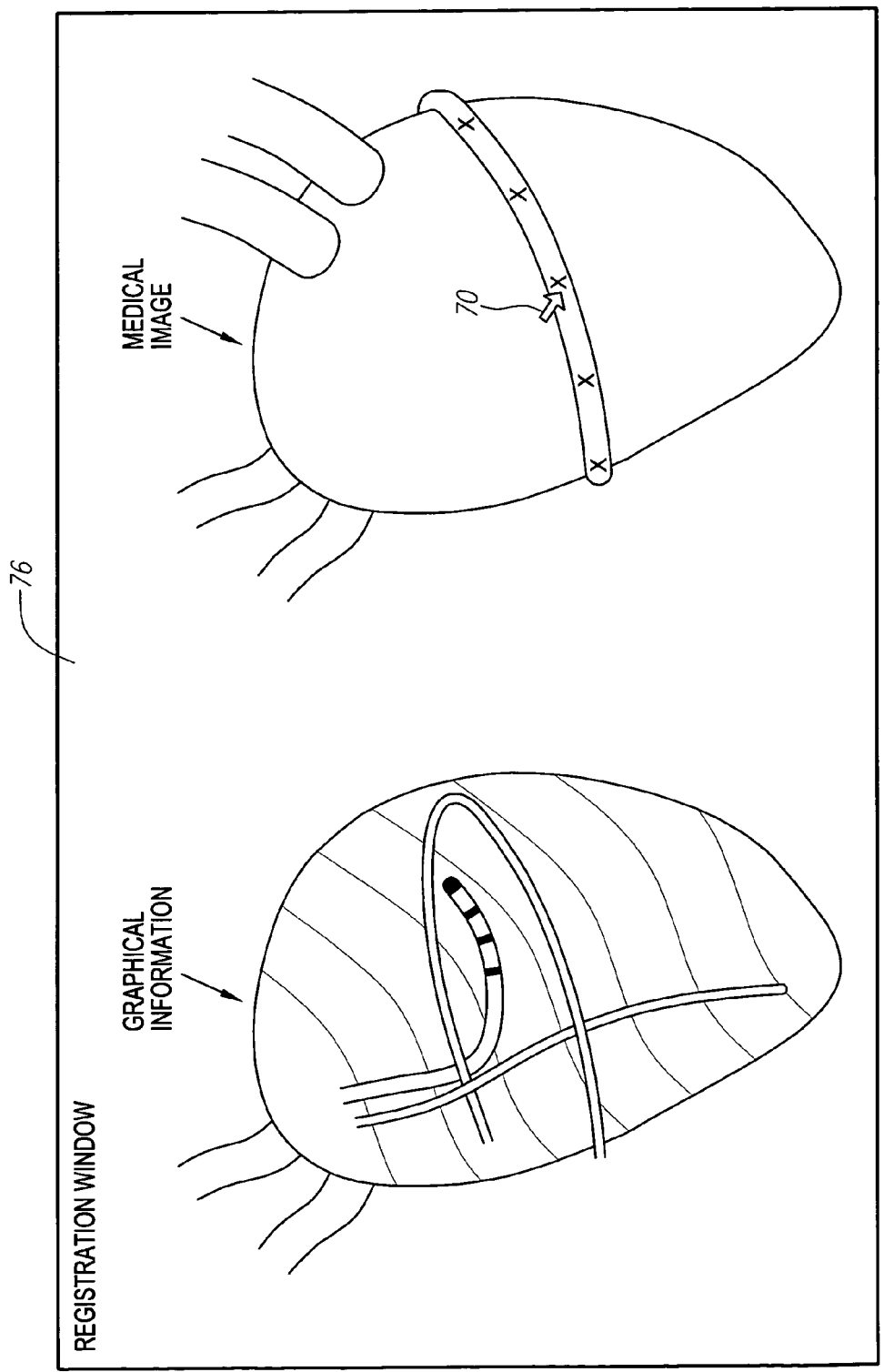
FIG. 7 is a display window that can be generated by the graphical user interface illustrated in FIG. 1, particularly illustrating a medical image acquired by the imaging subsystem and graphical information acquired by the three-dimensional graphics generator illustrated in FIG. 1 prior to merging within a composite medical image.

Referring still to FIG. 1, the imaging subsystem 14 is configured for generating three-dimensional image data of the heart, which can be displayed as a medical image, as illustrated in FIG. 7. Preferably, the three-dimensional image data generated by the imaging subsystem 14 is of a higher resolution than the graphical information that is reproduced by graphical reconstruction systems, such as the previously described RPM™ tracking and CARTO systems. In the illustrated embodiment, the imaging subsystem 14 comprises a Computed Tomography (CT) imager that generates cross-sectional image data slices of the heart and aggregates the data slices into high-resolution three-dimensional image data. Alternatively, a magnetic resonance imager (MRI) or a high-resolution ultrasound imager, such as the SONOS 7500 imaging system, marketed by Philips Medical System located in Bothell, Wash., can be used. The imaging subsystem 14 preferably comprises an external imaging device, such as a CT or MRI imager, but may comprise an internal imaging device, such as an intracardiac imaging catheter or transesophageal imaging probe, as long as the resulting images have the desired resolution. In any event, the image data generated by the imaging subsystem 14 is arranged in a three-dimensional image coordinate system that will subsequently be registered with the three-dimensional navigational coordinate system, as will be described in further detail below.

III. Graphical Navigation Subsystem

Referring still to FIG. 1, the graphical navigation subsystem 16 generally comprises (1) a plurality of ranging elements functionally divided into reference elements 34 and location elements 36; (2) ranging circuitry 38 configured for determining distances between various combinations of the reference and location elements 34, 36 in the form of time data; and (3) a three-dimensional registration processor 40 configured for determining the locations of the reference and location elements 34, 36 within the navigational coordinate system based on the time information provided by the ranging circuitry 38. In the illustrated embodiment, the navigation subsystem 16 is ultrasound-based, in which case, the reference and location elements 34, 36 take the form of ultrasound transducers, and the ranging circuitry 38 takes the form of a ultrasound ranging circuitry 38. Alternatively, the navigation subsystem 16 may be based on any other form of energy that can be wirelessly transmitted, such as magnetic or electrical energy.

A. Ranging Elements

Figure 2:
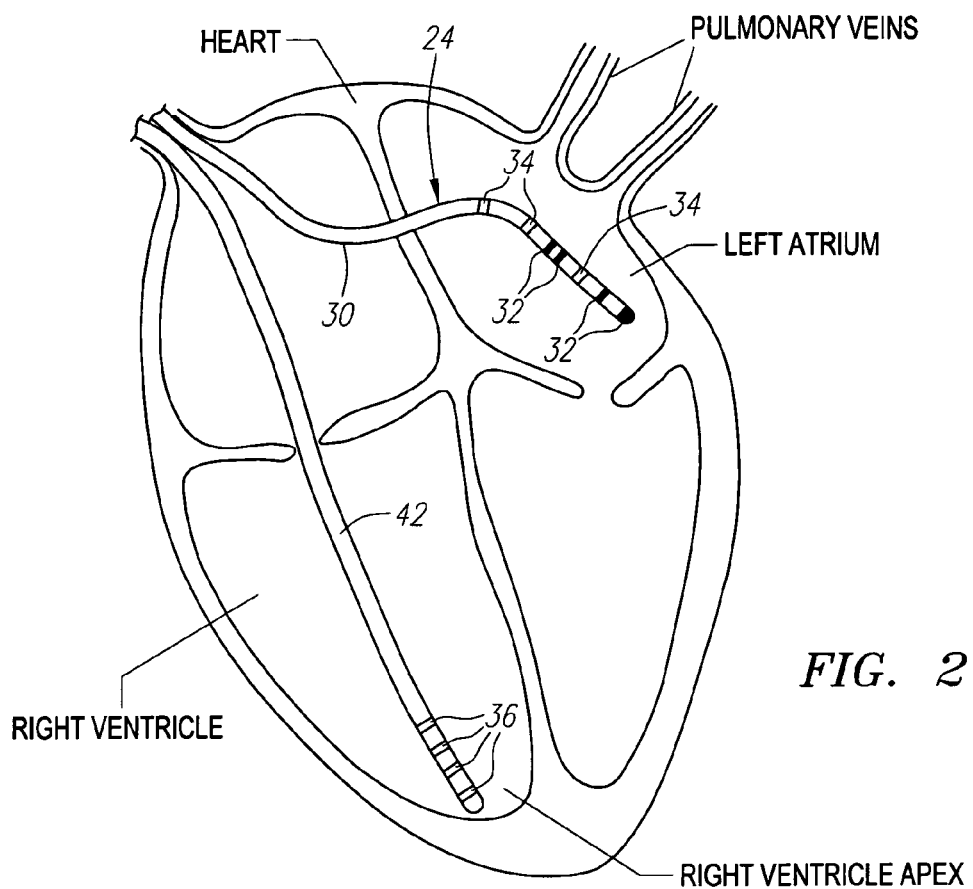
FIG. 2 is a cross-sectional view of a heart with a mapping/ablation catheter disposed in the left atrium and a reference catheter disposed within the right ventricle.
Figure 3:
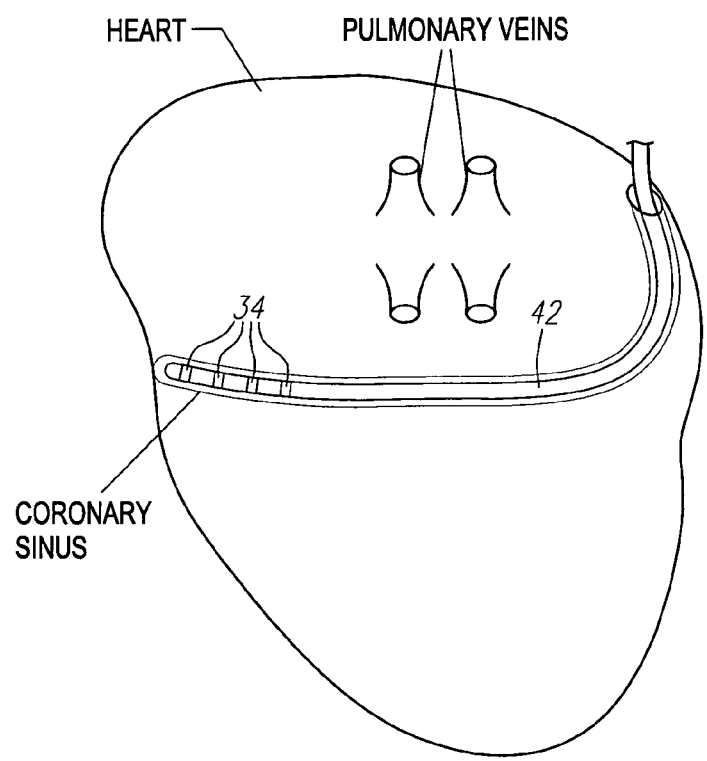
FIG. 3 is a cross-sectional view of a heart with a reference catheter disposed within the coronary sinus.

The reference elements 34 are mounted on a pair of reference catheters 42. In the illustrated embodiment, the number of reference elements 34 total eight, with four elements mounted on each reference catheter 42. The reference catheters 42 can be placed anywhere within the body (preferably, a known location) that arranges the reference elements 34 in three-dimensional space to establish the three-dimensional navigational coordinate system, and that allows the reference elements 34 to communicate with each other as well as with the location elements 36. For example, as illustrated in FIGS. 2 and 3, the first two dimensions of the coordinate system are provided by placing one of the reference catheters 42 (the "CS reference catheter") within the coronary sinus of the heart to arrange its four reference elements 34 in a two-dimensional plane, and the third dimension is provided by placing by placing the other reference catheter (the "RV reference catheter") within the right ventricular apex of the heart to arrange its four reference elements 34 off of the two-dimensional plane. It should be noted that only three of the reference elements 34 located on the CS reference catheter 42 are needed to provide the first two dimensions of the coordinate system, while only one of the reference elements 34 located on the RV reference catheter 42 is needed to provide the third dimension. The remaining reference elements 34 are redundant and are used to improve the accuracy of the triangulation process. As will be described in further detail below, the CS reference catheter 42, in addition to being used to establish the navigational coordinate system, will be advantageously used as a reference to register the image and navigation coordinate systems.

The location elements 36 are mounted at the distal end of a mapping/ablation catheter 24 (shown in FIG. 2), the first of which is mounted just proximal to the tip electrode 32, the second of which is mounted more proximally on the distal end, and the third of which is mounted proximal to the deflectable portion of the catheter. As will be described in further detail below, the location elements 36 facilitate the mapping of electrophysiological information within the heart, as well as the graphical representation and tracking of the mapping/ablation catheter 24. Although the medical image will be used for navigation, the location elements 36 optionally facilitate structural mapping of the endocardial surface of the heart chamber as the mapping/ablation catheter 24 is moved around within the chamber. Further details on the use of location elements 36 within the heart are described in U.S. Pat. No. 6,490,474 and U.S. patent application Ser. No. 09/128,304, entitled "A dynamically alterable three-dimensional graphical model of a body region," which are fully and expressly incorporated herein by reference.

B. Ranging Circuitry

The ultrasound ranging circuitry 38 is configured for conditioning the location elements 36 as receivers, i.e., to receive ultrasound pulses, and for conditioning the reference elements 34 as transceivers, i.e., to both transmit and receive ultrasound pulses. As can be appreciated, ultrasound transducers can be operated as transmitters by stimulating them with electrical pulses, which in turn causes the transducers to vibrate and transmit ultrasound pulses. Ultrasound transducers can be operated as receivers by receiving electrical pulses that are induced by the receipt of ultrasound pulses and subsequent vibration of the transducers.

The ultrasound ranging circuitry 38 is configured for measuring the distances between the reference elements 34 by conditioning each reference element 34 to transmit an ultrasound pulse, and conditioning the remaining reference elements 34 to receive that ultrasound pulse. The ultrasound ranging circuitry 38 then measures the "time-of-flight", i.e., the transit time, for each ultrasound pulse. As will be described in further detail below, the registration processor 40 will calculate distances from this time information, which can then be triangulated in order to establish the navigational coordinate system. The ultrasound ranging circuitry 38 is also configured for measuring the distances between the reference elements 34 and the location elements 36 by conditioning each of the reference elements 34 to transmit an ultrasound pulse, and conditioning the location elements 36 to receive this ultrasound pulse. The ultrasound ranging circuitry 38 then measures the time-of-flight for each ultrasound pulse.

Figures 4, 5:
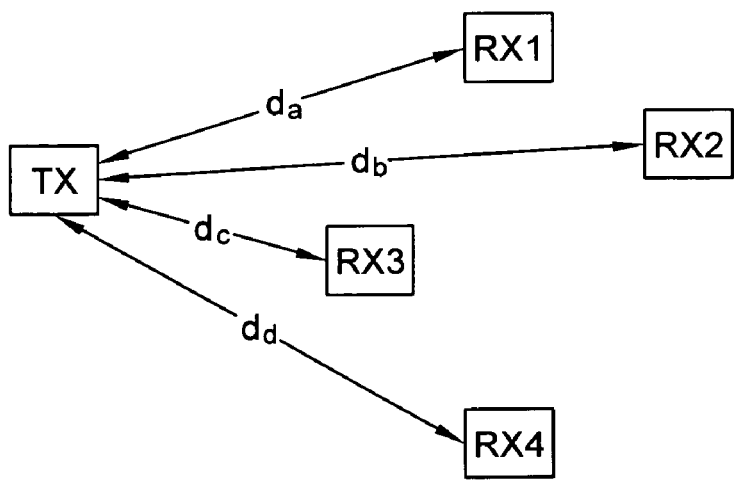
FIG. 4 is a table illustrating a distance matrix formed by calculating the distances between the location and reference elements illustrated in FIG. 1.
FIG. 5 is a functional block diagram of a positional arrangement between a plurality of ultrasound receiving transducers and an ultrasound transmitting transducer.

As will be described in further detail below, the registration processor 40 will calculate distances from this time information, which can then be triangulated in order to determine the positions (x, y, z) of the reference and location elements 34, 36 and thus any structure or tissue adjacent the reference and location elements 34, 36, within the established navigational coordinate system. Thus, it can be seen from FIG. 4 that an eight-by-eleven distance matrix, which is defined by the eight transmitting transducers on one side (eight reference elements 34 (TXVR1-8) and eleven receiving transducers on the other side (eight reference elements 34 (TXVR1-8) and three location elements 36 (RX1-3) located on the mapping catheter), is formed. This matrix contains the transit time of the ultrasound pulses transmitted between each transmitting transducer and the respective receiving transducers. As will be described in further detail below, the distances (d1-d80) between the respective transducers can then be calculated using these transit time values.

Further details regarding the structure and function of the ultrasound ranging circuitry 38 are disclosed in U.S. Pat. No. 6,216,027 and U.S. patent application Ser. No. 10/444,165, entitled "Method and System for Registering Ultrasound Image in Three-Dimensional Coordinate System," which are expressly incorporated herein by reference.

C. Three-Dimensional Registration Processor

Referring back to FIG. 1, the three-dimensional registration processor 40 is configured for registering the reference and location elements 34, 36 within the three-dimensional navigational coordinate system. In performing its registration function, the registration processor 40 first determines the distances between all of the reference and location elements 34, 36 based on the transit time matrix illustrated in FIG. 4 and a simple distance equation. For example, referring to FIG. 5, a transmitting transducer TX and four receiving transducers RX(1)-(4) are shown being separated from each other by respective distances $d_a$-$d_d$. To measure the distances $d_a$-$d_d$ between the transmitting transducer TX and the receiving transducers RX(1)-(4), the equation $d=v\tau$ can be used, where v is the velocity of the ultrasound pulse transmitted by the transmitting transducer TX through the medium to the receiving transducers RX(1)-(4), and τ is the time that it takes for the ultrasound pulse to travel between the transmitting transducer TX and the respective receiving transducer RX. To simplify the distance computation, the velocity of the ultrasound pulses may be assumed to be constant. This assumption typically only produces a small error, since the velocity of ultrasound pulses (estimated to be 1540 m/s) varies little in solid body tissue and blood.

Once the distances are known, the registration processor 40 then establishes the navigational coordinate system, which determination also includes coordinates of the reference elements 34 within the navigational coordinate system, by triangulating the relative distance calculations between each reference element 34 and the remaining reference elements 34. The registration processor 40 then determines the coordinates of the location elements 36 within this navigational coordinate system by triangulating the relative distance calculations between each of the location elements 36 and the reference elements 34. Preferably, the registration processor 40 determines the coordinates of the reference and location elements 34, 36 continually and in real time. In the illustrated embodiment, these coordinates are determined 15 times/second.

Additional details on this registration technique can be found in U.S. Pat. No. 6,490,474 and U.S. patent application Ser. No. 09/128,304, which have been previously incorporated herein by reference.

IV. Three-Dimensional Graphics Generator

Figure 6:
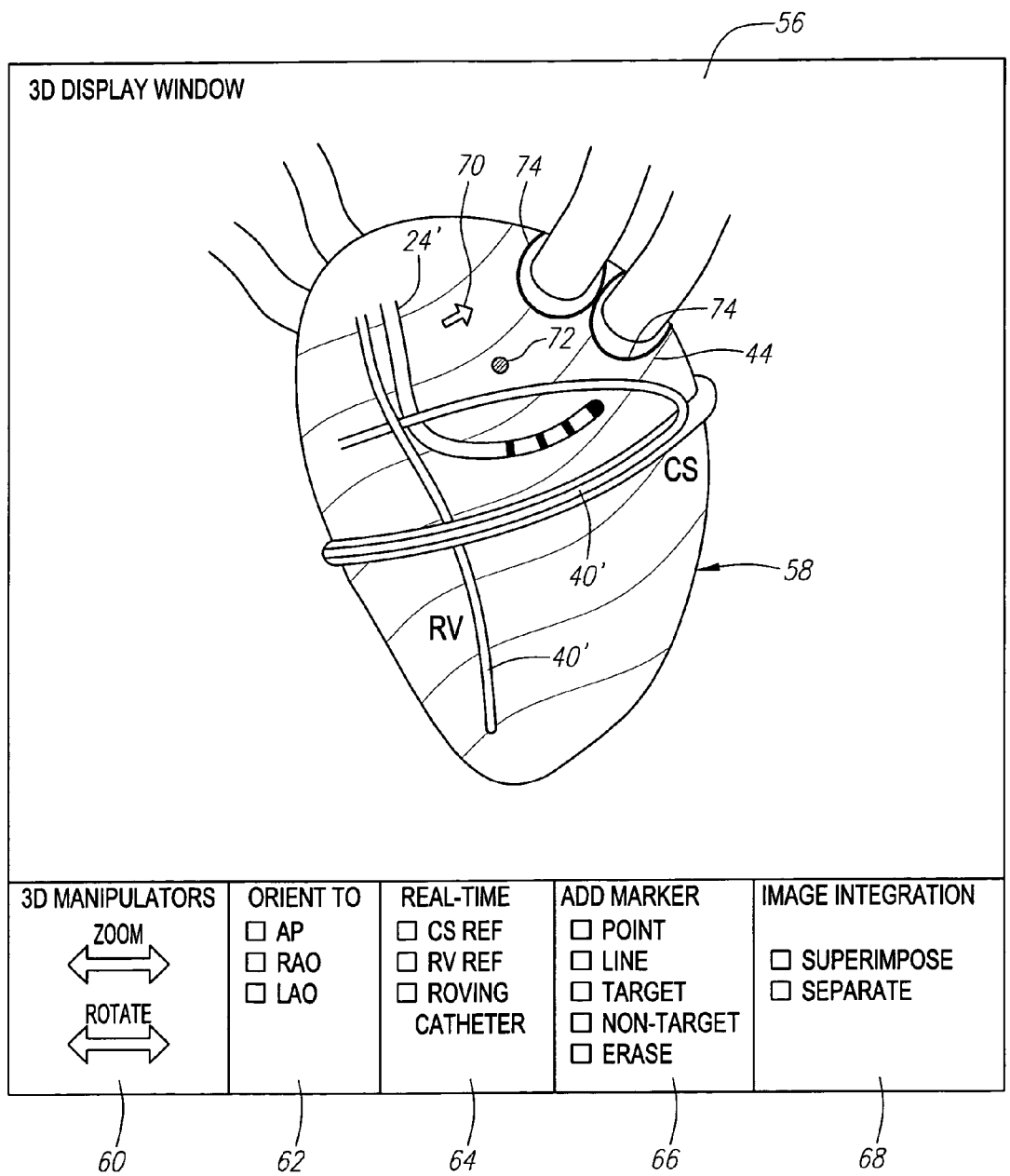
FIG. 6 is a display window that can be generated by the graphical user interface illustrated in FIG. 1, particularly illustrating a composite medical image formed by merging a medical image acquired by the imaging subsystem and graphical information acquired by the three-dimensional graphics generator illustrated in FIG. 1.

The graphics generator 18 generates three-dimensional graphical information, which in the illustrated embodiment, can be displayed as graphic representations 24', 40' of the respective mapping/ablation catheter 24 and reference catheters 42, and an electrophysiology (EP) map 44 of sensed electrical activity of the heart, as can be seen in FIG. 6.

The graphics generator 18 generates the graphical catheter representations 24', 40' from pre-stored graphical models of the catheters 24, 40, which can be deformed in accordance with the coordinates of the location elements 36 acquired from the three-dimensional registration processor 40. In the illustrated embodiment, the graphical catheter representations 24', 40' are dynamically generated in real-time. That is, the catheter representations are graphically generated in successive time periods (e.g., once every heartbeat), so that they move and bend as the actual catheters are moved and bent within the heart.

The graphics generator 18 generates the EP map 44, which may be, e.g., an isochronal or isopotential map) based on the EP data acquired from the mapping/ablation subsystem 12, which is temporally matched up with the coordinates of the mapping elements 32 as the mapping/ablation catheter 24 is moved from site-to-site. Thus, each EP measurement contains the physiological data for that site as well as the corresponding coordinates of that site. The coordinates of the mapping elements 32 can be obtained by geometrically extrapolating the coordinates of the location elements 36 acquired from the three-dimensional registration processor 40 based on the known geometry of the mapping/ablation catheter 24. This EP map illustrates sites of interest, e.g., electrophysiology recording and ablation sites, for providing subsequent ablative treatment. Details regarding the generation of EP maps based on the acquisition of EP data and corresponding location information are well known and will thus not be described here.

Although the imaging subsystem 14 generates high-resolution image data of the heart, the graphics generator 18 may optionally be configured for generating a graphical representation of the heart chamber (not shown). The graphics generator accomplishes this by deforming a graphical anatomical shell to the tip of the mapping/ablation catheter 24 as it is moved around in the heart chamber. The coordinates of the catheter tip can be obtained by geometrically extrapolating the coordinates of the location elements 36 acquired from the three-dimensional registration processor 40 based on the known geometry of the mapping/ablation catheter 24.

Additional details on graphically generating anatomical structures, catheters, and electrical activity maps within a three-dimensional environment can be found in U.S. Pat. No. 6,490,474 and U.S. patent application Ser. No. 09/128,304, which have previously been incorporated herein by reference.

V. Graphical User Interface

The graphical user interface 22 comprises (1) a user output device 46, and in particular a monitor, for displaying information to the user; (2) a user input device 48, and in particular a standard keyboard 50 and a graphical pointing device 52, such as a mouse, configured for allowing the user to interact with the information displayed on the monitor 46; and (3) a graphical processor 54 configured for displaying information on the monitor 46.

The graphical processor 54 is configured for acquiring composite image information from the image merger 20, which is arranged in a three-dimensional coordinate system, and displaying this information as a composite image 58 in a display window 56 (shown in FIG. 6) on the two-dimensional monitor 46. Techniques used to display three-dimensional data in a two-dimensional format are well known and will thus not be described in detail herein. As will be described in further detail below, the composite image information acquired from the image merger 20 comprises the medical information data generated by the imaging subsystem 14 and the graphical information generated by the three-dimensional navigation subsystem 16.

The graphical processor 54 responds to the user input device 48 by manipulating the composite image 58 within the display window 56. As an example, the user may rotate the display window 56 in three-dimensions and "zoom" towards or away from the window 56 by clicking on the appropriate icon in the manipulation box 60 using the mouse 52. The user may also select one of the standard orientations, used in fluoroscopy, such as anterior-posterior (AP), lateral, right anterior oblique (RAO) or left anterior oblique (LAO) by selecting the appropriate icon in orientation box 62 using the mouse 52. The user may also select which catheters to display in real-time by checking the appropriate icons in the real-time box 64 using the mouse 52.

Using the mouse 52, the user can also mark anatomical regions of interest on the composite image 58 by placing a cursor 70 at the appropriate location on the image 58 and clicking. As the marks are being made by the user, the graphical processor 54 transforms the x-y coordinate system of the cursor 70 into the three-dimensional coordinate system of the composite image using standard coordinate transformation techniques, so that the graphical processor 54 can superimpose the marks over the composite image 58. In the illustrated embodiment, the user can either mark the heart image 58 with point markings 72 or with line markings 74 (either linear or curvilinear).

For example, if the user desires to place a point marking 72 at an anatomical region of interest, the appropriate icon in the marking box 66 can be clicked, and then the user can mark the composite image 58 by moving the cursor 70 to a selected region on the image 58 and clicking the mouse 52. The composite image 58 can be marked with additional points markings 72 in the same manner. If the user desires to place a line marking 74 at an anatomical region of interest, the appropriate icon in the marking box 66 can be clicked, and then the user can mark the composite image 58 by clicking the mouse 52, and dragging the cursor 70. The user may also erase marks 72, 74 from the composite image 58 by clicking on the appropriate icon in the marking box 66, and them moving the cursor 70 over the mark 72, 74, while clicking the mouse 52.

The user may also designate the marked anatomical regions as either tissue that is targeted for treatment (in this case, ablation) or tissue that is not targeted for treatment—typically tissue that should not be ablated. In particular, prior to marking the composite image 58 as previously described, the user determines whether an anatomical region is targeted tissue or non-targeted tissue, and then clicks the appropriate icon in the marking box 66. Marks designating targeted tissue and marks designating non-targeted tissue can be distinguished from each other in order to remind the user during the ablation procedure which anatomical regions are to be ablated and which anatomical regions are not to be ablated. For example, marks designating targeted tissue can be generated and displayed with a particular color, such as green, to indicate that the corresponding anatomical regions are safe, and in fact, desirable, to ablate. Marks designating non-targeted tissue can be generated and displayed with another color, such as red, to indicate the corresponding anatomical regions are not safe to ablate. In the example illustrated in FIG. 6, the line markings 74 may designate targeted regions around the pulmonary veins, and the point marking 72 may designate non-targeted tissue, e.g., around the mitral valve.

The user, by clicking on the appropriate icon in the image integration box 68, can cause the graphical information and medical image data to be superimposed into the composite image 58, as illustrated in the display window 56 of FIG. 6, or separate the graphical information and medical image data to form separate graphical images and medical images, as illustrated in the registration window 76 of FIG. 7.

VI. Image Merger

As briefly discussed above, the image merger 20 superimposes the graphical information acquired from the three-dimensional navigation subsystem 16 and the medical image data acquired from the imaging subsystem 14, which when displayed, forms the composite medical image 58 displayed in the display window 56 of the monitor 46 illustrated in FIG. 6. The image merger 20 accomplishes this by registering the three-dimensional image coordinate system in which the medical image data is arranged and the three-dimensional navigational coordinate system in which the graphical information is arranged. In the illustrated embodiment, the navigational coordinate system is registered to the image coordinate system, so that the graphical information is superimposed over the medical image. However, the image coordinate system can alternatively be registered to the navigational coordinate system, so that the medical image is superimposed over the graphical information.

In registering the coordinate systems, the image merger 20 is configured for correlating the location of a physical structure within the navigational coordinate system with the location of an image of the physical structure within the image coordinate system, and then transforming the navigational coordinate system into the image coordinate system based on this correlation.

In particular, the same reference catheter that is used to establish the three-dimensional navigational coordinate system is also used to determine the location of the physical structure within the navigational coordinate system for purposes of transforming the two coordinate systems. In the illustrated embodiment, the physical structure is an anatomical structure that can be spatially correlated with the reference elements in an accurate manner. In this case, the anatomical structure is the coronary sinus of the heart, and thus, the reference catheter used to determine the geometry and location of the coronary sinus within the navigational coordinate system is the CS reference catheter 42. Notably, the coronary sinus provides an excellent landmark, because it has a well-defined two-dimensional geometry that facilitates correlation with the image of the coronary sinus in the medical image. In addition, the nature of the coronary sinus allows the CS reference catheter to easily conform to the shape of the coronary sinus. As such, the shape and location of the coronary sinus within the navigational coordinate system assumes the shape and location of the CS reference catheter 42 within the navigational coordinate system, which has already been determined for the purposes of generating the graphical catheter representation 42'.

In the illustrated embodiment, the location of the coronary sinus within the image coordinate system is determined by displaying and electronically marking the medical image in the registration window 76 of the monitor 46 with the cursor 70 in a manner similar to that discussed above with respect to the markings 72, 74. In this case, the image of the coronary sinus is marked with several x's using the cursor 70, as illustrated in FIG. 7. As the marks are being made on the medical image by the user, the graphical processor 54 transforms the x-y coordinate system of the cursor 70 into the three-dimensional image coordinate system using standard coordinate transformation techniques, so that the location of the coronary sinus image within the image coordinate system is determined.

Alternatively, the image merger 20 is configured for automatically locating the coronary sinus within the image coordinate system by processing the medical image data. Image segmentation techniques well known in the art can be used to identify the image data representing the coronary sinus in the medical image.

With knowledge of the location of the physical coronary sinus within the navigational coordinate system and the location of the coronary sinus image within the image coordinate system, which can be determined manually or automatically as described above, the image merger 20 can calculate a coordinate transformation function that can be used to transform the navigational coordinate system into the image coordinate system. In particular, a procrustean similarity transformation is used to perform the coordinate transformation. In general, this method determines the optimal rigid body transformation for matching two corresponding sets of points defined in separate coordinate systems. Further details describing the use of procrustean similarity transformations are set forth in "Studies in the Robustness of Multidimensional Scaling: Procrustes Statistics, Robin Simon, J. R. Statist, Soc. B (1978), 40, No. 2, pp. 234-238. The procrustean similarity transformation can be applied to the navigational and image coordinate systems as follows.

A configuration X of N points in the navigational coordinate system can be represented by a 3×N matrix: $X=[x^{(1)}, \ldots x^{(N)}]$, and a configuration Y of N points in the image coordinate system can be represented by a 3×N matrix: $Y=[y^{(1)}, \ldots y^{(N)}]$, where $x^{(i)}$ and $y''^{(i)}$ correspond to the same physical structure defined in the two different coordinate systems. Also, $X_0$ and $Y_0$ can be the origin centered translations of X and Y. That is, $X_0 = X - \overline{X} 1_N^T$ and $Y_0 = Y - \overline{Y} 1_N^T$, where $$\overline{X} = \frac{1}{N} \sum_{i=1}^{N} x^{(i)},$$

and $$\overline{Y} = \frac{1}{N} \sum_{i=1}^{N} y^{(i)}.$$

The optimal (in a least squares sense) rigid body transformation for matching the points in X to those of Y is given by: $VU^T(X - \overline{X 1_N^T}) + \overline{Y} 1_N^T$, where $X_0 Y_0^T = U\Sigma V^T$. That is, U, $V^T$ are singular vectors of the singular value decomposition of $X_0 Y_0^T$.

The image merger 20 is configured for applying the coordinate transformation function to the graphical information, and merging the medical image data with the transformed graphical information to generate composite information that can be displayed by the graphic user interface 22 as a composite image 58.

Although the image merger 20 has been described as solely using the coronary sinus for registering the navigational and image coordinate systems and subsequently merging the medical image data and graphical information, it can be appreciated that the locations of additional physical structures can be correlated between the navigational and image coordinate systems to improve the accuracy of the coordinate system registration and resulting merger of the graphical information and medical image. For example, the tip of the mapping/ablation catheter 24 can be moved around within the heart in order to locate well-defined physical structures, such as the ostium of a pulmonary vein, within the navigational coordinate system. The coordinate(s) of the additional physical structure can then be added to the coordinate(s) of the coronary sinus within the navigational coordinate system. The image of this additional physical structure can then be located within the medical image in the same manner that the image of the coronary sinus was located. The coordinate(s) of the image reference of the additional physical structure can then be added to the coordinate(s) of the coronary sinus image within the image coordinate system. Using the additional data points, the navigational and image coordinate systems can then be registered in the same manner described above.

It can be appreciated that not only does the use of reference catheters in the manner described above advantageously provide the dual function of both establishing a navigational coordinate system and registering that coordinate system with an image coordinate system, such use eliminates the need for the user to locate the anatomical structures within a graphical environment that may not accurately reflect the anatomical environment, thereby increasing the accuracy of the image coordinate registration while reducing the time otherwise spent attempting to locate the anatomical structures. This is especially true when the anatomical structure is one with which a reference catheter can be stably associated, such as the coronary sinus of the heart. The user need only electronically mark the anatomical structure in the image coordinate system, which in the case where the anatomical structure is a well-defined coronary sinus, can be easily accomplished. Of course, the user need not electronically mark the anatomical structure at all in the case where the anatomical structure is automatically located within the image coordinate system. In addition, it can be appreciated that the navigation of the mapping/ablation catheter 24 with reference to the medical image can occur as soon as the reference catheters 42 are in place within the heart, since registration of the coordinate systems is based on a known anatomical structure that need not be identified in the navigational coordinate system by reference to a graphical image.

It should be noted that although the physical structure that is correlated has been described as being an anatomical structure, and in particular, the coronary sinus of the heart, the physical structure can take the form of other structures that are correlated to the reference elements, such as the reference catheter or any portion of the reference catheter, including the reference elements themselves. In this case, the location of the reference catheter or reference elements within the navigational coordinate system will be correlated to the location of the image of the reference catheter or reference elements in the image coordinate system. Notably, the use of the reference catheter or reference elements as the physical structure whose location will be correlated between the coordinate systems will potentially provide a more accurate registration between the coordinate systems, since, in this case, the locations of the reference elements will not have to be extrapolated to determine the location and shape of adjacent anatomical structures. However, because medical images typically take the form of preoperative images that do not contain images of non-anatomical structures, such as catheter images, the only physical structure in such images that can be correlated is an anatomical structure, such as the coronary sinus of the heart.

Figure 8:
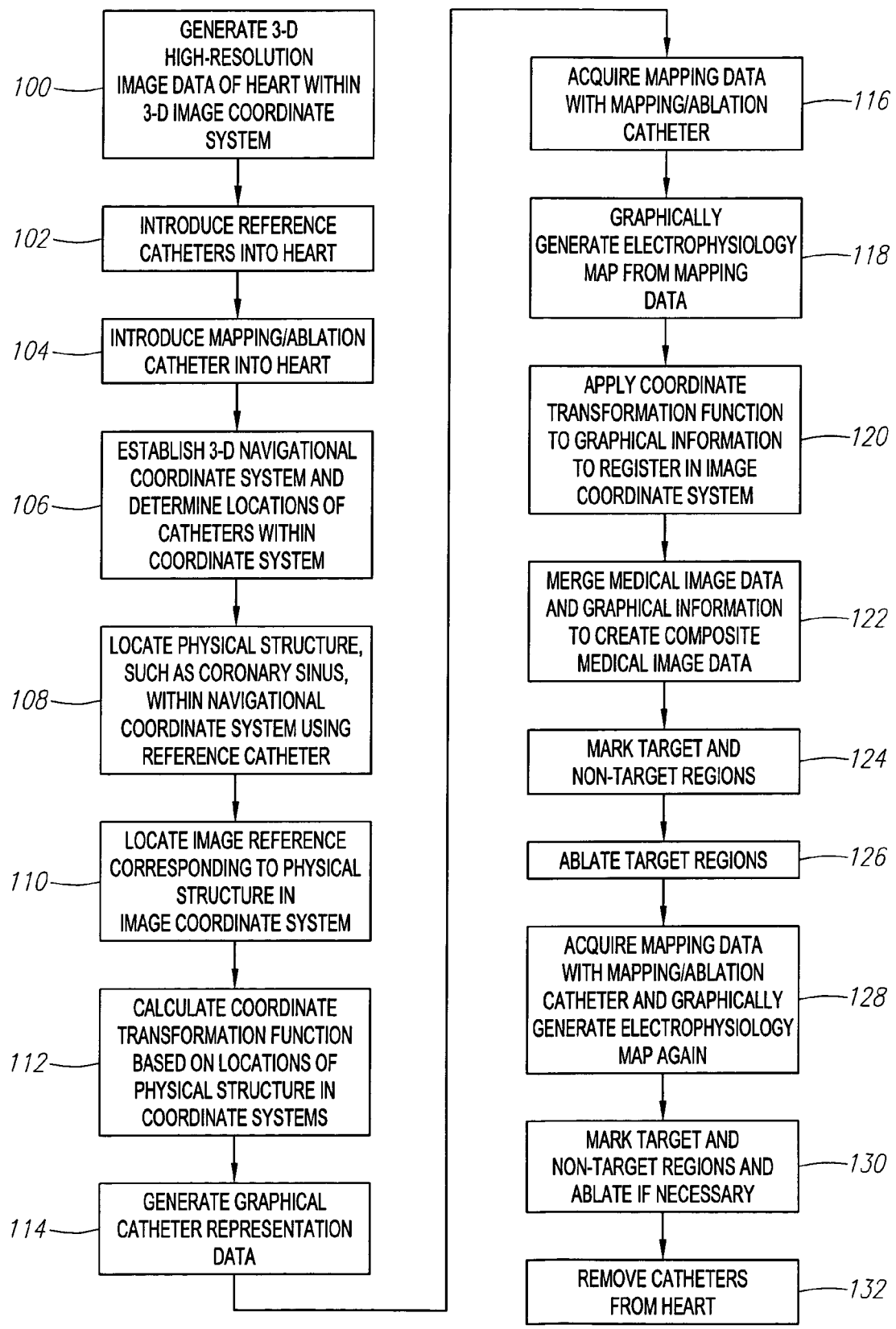
FIG. 8 is a flow diagram illustrating one method of diagnosing and treating atrial fibrillation using the medical system of FIG. 1.

Having described the structure of the medical system 10, one method of using the system 10 to locate and treat an aberrant conductive pathway within the heart, such as those typically associated with atrial fibrillation, will now be described with reference to FIG. 8. First, the imaging subsystem 14 is operated in order to acquire high-resolution medical image data of the patient's heart, which will be arranged in a three-dimensional image coordinate system (step 100).

In the illustrated method, the medical image data is preoperative and will thus not contain medical implements, such as catheters. As briefly discussed above, the imaging step may typically be performed at a different site than the site at which the procedure is performed, in which case, preoperative medical image data will be provided to the doctor. If the medical image data is acquired at a different site it can be transferred to the image merger 20 and graphical user interface 22, e.g., by downloading over the Internet, or storing on a computer medium, such as a compact disk, and loading directly into the system. It should be noted, however, that the imaging step can be alternatively or optionally be performed during the procedure to provide the doctor with real-time or near real-time medical image data. In this case, the medical image data can be transferred to the image merger 20 and graphical user interface 22 immediately and automatically upon acquisition.

Next, under fluoroscopy, the reference catheters 42 are intravenously introduced into the heart, and in particular, within the coronary sinus and right ventricular apex, so that the reference elements 34 are placed firmly in contact with the coronary sinus (step 102). Then, the mapping/ablation catheter 24 is introduced into the left atrium of the heart under fluoroscopy (step 104). Of course, the catheter 24 can be introduced into other chambers of the heart, such as the left ventricle, e.g., if the disease to be treated is ventricular tachycardia.

Then, the graphical navigation subsystem 16 is operated to transmit signals between the reference elements 42 and location elements 44 in order to establish the navigational coordinate system and determine the locations of the reference elements 42 and location elements 44 within the established navigational coordinate system (step 106). Once the navigational coordinate system is established and the locations of the reference elements 42 within the navigational coordinate system determined, the navigational and image coordinate systems are registered, so that the medical image data directly or indirectly acquired from the imaging subsystem 14 can be merged with any graphical information previously and subsequently acquired from the three-dimensional graphics generator 18.

In particular, the location of the coronary sinus within the navigational coordinate system is determined by extrapolating the determined locations of the reference elements 34 (step 108). If the medical image data contains an image of the reference catheter 42, the location of the reference catheter 42 within the navigational coordinate system can be determined to increase accuracy of the registration process. Of course, if medical image data contains an image of the reference elements 34, the locations of the reference elements 34 within the navigational coordinate system, which have already been determined, can be used in the coordinate registration process without extrapolation. Next, an image reference within the image coordinate system corresponding to the coronary sinus (or alternatively, the reference catheter or reference elements) is located (step 110). For example, the user may electronically mark the image reference, as illustrated in FIG. 7, or if the system 10 is so enabled, the image merger 20 can automatically location the image reference. Then, the image merger 20 is operated to register the image and navigational coordinate systems based on the determined location of the image reference within the image coordinate system and the determined location of the physical structure (coronary sinus, or alternatively the reference catheter or reference elements) within the navigational coordinate system. In particular, the image merger 20 calculates a coordinate transformation function (step 112).

Next, the three-dimensional graphics generator 18 may be operated to generate the graphical catheter representations 24,' 42' within the navigational coordinate system (step 114). Display of the graphical catheter representations 24', 42' is accomplished in real-time as the catheters are moved within the heart. The user may select which catheter representations 24', 42' are to be displayed using the real-time box 64 on the monitor 46. Next, the mapping processor 26 is operated to record electrical activity within the left atrium of the heart with the mapping/ablation catheter 24 and derive mapping data therefrom (step 116). The graphical processor 28 acquires this mapping data and generates the electrical activity map 42 within the navigational coordinate system (step 118). As the graphical information, such as the graphical catheter representations 24', 42' and EP map 44, is generated, the image merger 20 applies the coordinate transformation function to the data that makes up the graphical information (step 120), and merges the medical image data and graphical information to create the composite medical image 58 for display in the display window 56 of the monitor 46, as illustrated in FIG. 6 (step 122) The application of the transformation function occurs in real-time, so that the composite medical image 58 reflects movement of the catheter representations 24', 42'.

It should be appreciated that although the illustrated method is described as acquiring graphical information subsequent to the registration process, generation of the graphical information can occur prior to registration of the navigational and image coordinate systems. That is, the graphical information can be generated and displayed separately from the medical image, as illustrated in FIG. 7. Once registration occurs, the medical image data and graphical information can be merged to create the composite medical image 58 illustrated in FIG. 6.

If an aberrant region is identified, the user will then use the mouse 52 to graphically generate markings 72, 74 on the target and non-target ablation regions of the heart (step 124). The distal electrode 32 of the mapping/ablation catheter 24 is then placed into contact with the targeted tissue, and the RF generator 28 operated to therapeutically create a lesion (step 126). If the targeted tissue mark is a point marking 72 or a series of point markings 72, the lesion will take the form of a spot lesion or lesions. If the targeted tissue mark is a line marking 74, the lesion will take the form of a linear or curvilinear lesion. After the ablation process is complete, the mapping processor 26 can again be operated to ensure that the heart disease has been successfully treated by reacquiring the mapping data and regenerating the EP map 44, which will be merged with the medical image data to create a renewed composite medical image 58 for display on the display window 56 of the monitor 46 (step 128). If additional aberrant conductive pathways have been found, the marking and ablation steps can be repeated (step 130). If no aberrant conductive pathways have been found, the reference catheters 42 and mapping/ablation catheter 24 can then be removed from the heart (step 132).

Although particular embodiments of the present invention have been shown and described, it will be understood that it is not intended to limit the present invention to the preferred embodiments, and it will be obvious to those skilled in the art that various changes and modifications may be made without departing from the spirit and scope of the present invention. Thus, the present inventions are intended to cover alternatives, modifications, and equivalents, which may be included within the spirit and scope of the present invention as defined by the claims.

What is claimed is:

1. A method of processing a medical image of an anatomical body containing image data arranged in an image coordinate system, the method comprising:

placing at least one of a plurality of reference elements into contact with an anatomical structure;

transmitting signals between the reference elements to establish a navigational coordinate system internal to the anatomical body and to determine locations of the at least one reference element within the navigation coordinate system;

determining the location of an anatomical structure within the navigational coordinate system based on the determined locations of the at least one reference element within the navigation coordinate system;

determining the location of an image reference corresponding to the anatomical structure within the image coordinate system; and registering the navigational and image coordinate systems based on the determined location of the anatomical structure within the navigational coordinate system and the determined location of the image reference within the image coordinate system.

2. The method of claim 1, wherein the image is a preoperative image.

3. The method of claim 1, wherein the image is a computed tomography (CT) image.

4. The method of claim 1, wherein the reference elements are placed inside of the anatomical body.

5. The method of claim 1, wherein the anatomical body is a heart.

6. The method of claim 5, wherein the anatomical structure is the coronary sinus of the heart, and at least one of the reference elements is placed within the coronary sinus.

7. The method of claim 1, wherein the reference elements are carried by at least one catheter.

8. The method of claim 1, wherein the navigational coordinate system is a three-dimensional coordinate system.

9. The method of claim 1, wherein the reference elements are ultrasound transducers, and the transmitted signals are ultrasound signals.

10. The method of claim 1, wherein the navigational coordinate system is established based on times-of-flight of the transmitted signals.

11. The method of claim 1, wherein the location of the anatomical structure within the navigational coordinate system is determined based on the determined locations of the reference elements within the navigational coordinate system.

12. The method of claim 11, further comprising:
moving a location element within the anatomical body;
transmitting signals between the reference elements and the location element to determine the location of the location element within the navigational coordinate system;
determining the location of another anatomical structure within the navigational coordinate system based on the determined location of the location element within the navigational coordinate system;
determining the location of another image reference corresponding to the other anatomical structure within the image coordinate system; and
wherein the navigational and image coordinate systems are registered further based on the determined location of the other anatomical structure within the navigational coordinate system and the determined location of the other image reference within the image coordinate system.

13. The method of claim 1, wherein the image reference location determination comprises displaying the medical image and electronically marking the displayed image reference.

14. The method of claim 13, wherein the displayed image reference is electronically marked by using a cursor.

15. The method of claim 1, wherein the image reference location determination comprises automatically identifying image data corresponding to the image reference.

16. The method of claim 1, wherein the coordinate system registration comprises calculating a coordinate transformation function and applying the coordinate transformation function to one of the image and navigational coordinate systems.

17. The method of claim 1, further comprising:
moving a catheter within the anatomical body; and
transmitting signals between a location element carried by the catheter and the reference elements to determine the location of the catheter within the navigational coordinate system.

18. The method of claim 1, wherein the at least one reference element is affixed relative to the anatomical structure.

19. A medical system for processing a medical image of an anatomical body containing image data arranged in an image coordinate system, the system comprising:
one or more catheters carrying a plurality of reference elements;
control circuitry configured for conditioning the reference elements to transmit signals between each other; and
one or more processors configured for establishing a navigational coordinate system based on the transmitted signals, determining locations of at least one of the reference elements within the navigational coordinate system, determining the location of an anatomical structure within the navigational coordinate system based on the determined locations of the at least one reference element within the navigation coordinate system, determining the location of an image reference corresponding to the anatomical structure within the image coordinate system, and registering the navigational and image coordinate systems based on the determined location of the anatomical structure within the navigational coordinate system and the determined image reference within the image coordinate system.

20. The system of claim 19, further comprising an imaging system configured for generating the medical image.

21. The system of claim 20, wherein the imaging system comprises a computed tomography (CT) imager.

22. The system of claim 19, wherein the navigational coordinate system is a three-dimensional coordinate system.

23. The system of claim 19, wherein the reference elements are ultrasound transducers, and the transmitted signals are ultrasound signals.

24. The system of claim 19, wherein the control circuitry comprises ranging circuitry.

25. The system of claim 19, wherein the one or more processors determines the location of the anatomical structure within the navigational coordinate system based on the determined locations of the at least one reference element within the navigational coordinate system.

26. The system of claim 25, further comprising:
a catheter carrying a location element;
control circuitry configured for conditioning the reference elements and location element to transmit signals between each other;
wherein the one or more processors is configured for determining the location of another anatomical structure within the navigational coordinate system based on the location of location element within the navigational coordinate system, determining the location of another image reference corresponding to the other anatomical structure within the image coordinate system, and registering the navigational and image coordinate systems further based on the determined location of the other anatomical structure within the navigational coordinate system and determined location of the other image reference within the image coordinate system.

27. The system of claim 19, wherein the one or more processors is configured for determining the location of the image reference in response to an electronic mark made by a user.

28. The system of claim 27, wherein the one or more processors is configured for allowing the electronic mark to be made by the user with a cursor.

29. The system of claim 19, wherein the one or more processors is configured for determining the location of the image reference by automatically identifying image data corresponding to the image reference.

30. The system of claim 19, wherein the one or more processors is configured for registering the navigational and image coordinate systems by calculating a coordinate transformation function and applying the coordinate transformation function to one of the image and navigational coordinate systems.

31. The system of claim 19, further comprising a functional catheter carrying a location element, wherein the control circuitry is configured for conditioning the location and reference elements to transmit signals between each other, and the one or more processors is configured for determining the location of the functional catheter within the navigational coordinate system based on the transmitted signals.

32. A method of superimposing a medical image of an anatomical body and graphical information, the medical image containing image data arranged in an image coordinate system, the method comprising:
   placing a reference catheter in contact with an anatomical structure;
   moving a functional catheter within the anatomical body;
   acquiring location information with the functional catheter by transmitting signals between the reference and functional catheters;
   generating the graphical information based on the location information;
   determining a location of the reference catheter;
   locating the anatomical structure based on the determined location of the reference catheter;
   using the reference catheter to establish a graphical coordinate system, whereby the location of the anatomical structure within the graphical coordinate system is determined;
   identifying an image reference corresponding to the anatomical structure;
   determining the location of the image reference within the image coordinate system; and
   merging the graphical information and medical image based on the located anatomical structure and the identified image reference by registering the graphical and image coordinate systems based on the determined location of the anatomical structure within the graphical coordinate system and determined location of the image reference within the image coordinate system.

33. The method of claim 32, wherein the image is a preoperative image.

34. The method of claim 32, wherein the image is a computed tomography (CT) image.

35. The method of claim 32, wherein the anatomical body is a heart.

36. The method of claim 35, wherein the anatomical structure is the coronary sinus of the heart, and at least one of the reference elements is placed within the coronary sinus.

37. The method of claim 32, wherein the transmitted signals are ultrasound signals.

38. The method of claim 32, wherein the location information is determined based on times-of-flight of the transmitted signals.

39. The method of claim 32, further comprising moving the functional catheter within the anatomical body, wherein the location information is acquired during movement of the functional catheter within the anatomical body.

40. The method of claim 32, further comprising acquiring medical information with the functional catheter, and deriving the location of the medical information from the acquired location information, wherein the graphical information is generated from the acquired medical information.

41. The method of claim 40, wherein the medical information is electrophysiology (EP) data, and the graphical information is an EP map.

42. The method of claim 32, wherein the graphical information is generated subsequent to location of the anatomical structure.

43. The method of claim 32, wherein the graphical information comprises a representation of the functional catheter.

44. The method of claim 32, further comprising:
   locating another anatomical structure spatially correlated to the functional catheter;
   identifying another image reference corresponding to the other anatomical structure; and
   merging the graphical information and medical image further based on the other located anatomical structure and the other identified image reference.

45. The method of claim 32, wherein the identification of the image reference comprises displaying the medical image and electronically marking the displayed image reference.

46. The method of claim 45, wherein the displayed image reference is electronically marked by using a cursor.

47. The method of claim 32, wherein the identification of the image reference comprises automatically identifying image data corresponding to the image reference.

48. The method of claim 32, wherein the reference catheter is affixed relative to the anatomical structure.

49. A medical system for superimposing a medical image of an anatomical body and graphical information, wherein the medical image contains image data arranged in an image coordinate system, comprising:
   a reference catheter;
   a functional catheter;
   control circuitry configured for conditioning the reference and functional catheters to transmit signals between each other; and
   one or more processors configured for acquiring location information with the functional catheter based on the transmitted signals, determining a location of the reference catheter, locating an anatomical structure based on the determined location of the reference catheter, establishing a graphical coordinate system with the reference catheter, whereby the location of the anatomical structure within the graphical coordinate system is determined, generating the graphical information based on the location information, identifying an image reference corresponding to the anatomical structure, and merging the graphical information and medical image based on the located anatomical structure and the identified image reference by registering the graphical and image coordinate systems based on the determined location of the anatomical structure within the graphical coordinate system and the determined location of the image reference within the image coordinate system.

50. The system of claim 49, further comprising an imaging system configured for generating the medical image.

51. The system of claim 50, wherein the imaging system comprises a computed tomography (CT) imager.

52. The system of claim 49, wherein the transmitted signals are ultrasound signals.

53. The system of claim 49, wherein the control circuitry comprises ranging circuitry.

54. The system of claim 49, wherein the one or more processors are configured for acquiring medical information with the functional catheter, and deriving the location of the medical information from the acquired location information, wherein the graphical information is generated from the acquired medical information.

55. The system of claim 54, wherein the medical information is electrophysiology (EP) data, and the graphical information is an EP map.

56. The system of claim 49, wherein the one or more processors is configured for generating the graphical information subsequent to locating the anatomical structure.

57. The system of claim 49, wherein the graphical information comprises a representation of the functional catheter.

58. The system of claim 49, wherein the one or more processors is configured for locating another anatomical structure spatially correlated to the functional catheter, identifying another image reference corresponding to the other anatomical structure, and merging the graphical information and medical image further based on the other located anatomical structure and the other identified image reference.

59. The system of claim 49, wherein the one or more processors is configured for locating the image reference in response to an electronic mark made by a user.

60. The system of claim 59, wherein the one or more processors is configured for allowing the electronic mark to be made by the user with a cursor.

61. The system of claim 49, wherein the one or more processors is configured for automatically identifying the image reference.

* * * * *